United States Patent [19]
Stahl

[11] Patent Number: 5,304,202
[45] Date of Patent: Apr. 19, 1994

[54] METHOD AND APPARATUS FOR ENABLING INTRAVENOUS THERAPY WHEN CARDIAC OUTPUT IS LESS THAN USUALLY NECESSARY

[76] Inventor: Daniel A. Stahl, 7471 Fillmore St., Hollywood, Fla. 33024

[21] Appl. No.: 33,553

[22] Filed: Mar. 18, 1993

[51] Int. Cl.⁵ .............................................. A61B 17/12
[52] U.S. Cl. .................................... 606/203; 606/201
[58] Field of Search .................. 24/16 PB, 682, 683, 24/685; 128/57, 60, 61, 62 R, 67, 384, 677, 686; 206/805; 482/121, 124; 63/5.1; 602/53, 75; 604/115, 116; 606/201-204

[56] References Cited

U.S. PATENT DOCUMENTS

| | | |
|---|---|---|
| 515,367 | 9/1894 | Rounseville . |
| 832,352 | 10/1906 | Wallenthin .............................. 24/683 |
| 1,757,060 | 5/1930 | Rieth . |
| 2,068,173 | 1/1937 | Galves ................................... 606/203 |
| 2,091,131 | 8/1937 | Cone . |
| 2,258,720 | 10/1941 | Saighman ............................... 606/203 |
| 2,333,237 | 11/1943 | Erekson ................................. 606/203 |
| 2,461,201 | 2/1949 | Ellis ........................................ 63/5.1 |
| 2,511,269 | 6/1950 | Jones . |
| 3,156,243 | 11/1964 | Sculley .................................. 606/203 |
| 3,467,077 | 9/1969 | Cohen . |
| 3,570,495 | 3/1971 | Wright . |
| 3,586,001 | 6/1971 | Sanderson . |
| 3,587,584 | 6/1971 | Keller . |
| 3,654,931 | 4/1972 | Hazlewood . |
| 3,814,085 | 6/1974 | Kupchinski ............................. 128/57 |
| 4,066,084 | 1/1978 | Tillander . |
| 4,228,792 | 10/1980 | Rhys-Davies ......................... 606/203 |
| 4,566,436 | 1/1986 | Loefquist .............................. 606/203 |
| 4,664,651 | 5/1987 | Weinshenker et al. ............... 604/115 |
| 4,848,324 | 7/1989 | Gavriely ................................. 606/203 |

FOREIGN PATENT DOCUMENTS 237486  7/1925  United Kingdom ................ 606/202

*Primary Examiner*—Ralph Lewis
*Attorney, Agent, or Firm*—Jacobson, Price, Holman & Stern

[57] ABSTRACT

An elongated elastic cylindrical member joined at its opposite ends to form an annular member is provided. The annular member is designed for disposition about a body limb near the end thereof adjacent the torso and with the annular member circumferentially stretched and exerting a heavy radial inward pressure upon the limb at least substantially the full length of an elongated zone extending completely about the associated limb with the inward force of the annular member on the limb being sufficient to locally compress not only limb veins closely adjacent the skin surface but also arteries spaced further beneath the limb surface.

The method comprises hyperextending veins of the limb adjacent the free end thereof by gradually rolling the annular member downwardly along the limb toward the free end thereof with the heavy radial inward pressure upon the limb being sufficient to locally compress the veins and arteries of the limb beneath the annular member and to thereby "milk" both venous and arterial blood downwardly through the veins and the arteries of the limb, whereby at least one vein adjacent the end of the limb will be engorged with blood and sufficiently hyperextended for ease of location and insertion of a needle therein preparatory to intravenous therapy.

8 Claims, 1 Drawing Sheet

METHOD AND APPARATUS FOR ENABLING INTRAVENOUS THERAPY WHEN CARDIAC OUTPUT IS LESS THAN USUALLY NECESSARY

BACKGROUND OF THE INVENTION

1. Field of the Invention

When desiring to initiate intravenous therapy, a person rendering the therapy must find a vein on a patient into which a needle may be introduced for use in carrying out the desired intravenous therapy.

It is now common practice to use a rubber tourniquet applied about an upper portion of a body limb for the purpose of restricting venous return of blood from that limb to the torso. When cardiac output is sufficient, the veins distal to the tourniquet become hyperextended as they fill with blood that is being pumped to their connecting arteries of the veins. The hyperstatic pressure created by the heart forces the blood through the arteries that lie underneath the tourniquet. Blood continues through the arterioles, capillaries, venules, and then the veins distal to the tourniquet. The constricting band action of the tourniquet limits or prevents the return of that blood to the heart. Then a hypertensive action becomes apparent as the veins distal to the tourniquet become engorged with blood and hyperextended. It is at this time that a needle may be introduced into a hyperextended vein for the purpose of intravenous therapy.

However, when a patient has substantially no cardiac output, a tourniquet is not operative to cause a vein to be hyperextended in order to facilitate the starting of intravenous therapy. When substantially no cardiac output is present the veins are substantially collapsed and only the arteries of a body limb disposed considerably below skin surface have any appreciable amount of blood therein. Accordingly, in many instances, paramedics, nurses and doctors attempting to introduce a needle into a vein are unable to find such a vein. Of course, time lost in starting intravenous therapy under these conditions often is a matter of life or death. A doctor may try several minutes in a critical situation and then, as a last resort, attempt to introduce the needle into a femoral artery or perform a "cut down" (minor surgical procedure) or may do a subclavian. All of these procedures are time consuming and the accumulative loss in time may be critical.

Accordingly, a need exists for a means by which a suitable vein may be engorged with blood and thus hyperextended, even when the patient has little or no cardiac output.

2. Description of the Related Art

While there have been many different forms of tourniquets heretofore utilized, none of the previously used forms of tourniquets are operative, on a patient with substantially no cardiac output, to engorge a vein with blood so as to present a hyperextended vein into which a needle may be readily introduced for intravenous therapy. Examples of previously known forms of tourniquets and similar structures are disclosed in U.S. Pat. Nos. 1,757,060, 2,091,131, 2,511,269, 3,467,077, 3,570,495, 3,586,001, 3,587,584, 3,654,931 and 4,066,084.

The massaging apparatus disclosed in U.S. Pat. No. 2,091,131 comprises a roller assembly adapted to be encircled about a body limb such as an arm and to be rolled up and down the arm as a massaging device, the massaging device incorporating relative soft and porous rollers so as to massage and knead the body of the patient in a gentle manner, which massaging action is not effective to carry out the objects of the instant invention and which gentle manner is likewise ineffective to carry the objects of the instant invention.

Still further, U.S. Pat. No. 4,066,084 to Tillander is designed specifically to gradually upwardly compress circumferential zones of a body limb in order to empty blood from the limb extremity toward the heart of a patient prior to surgical incision. Inasmuch as this apparatus is designed to empty the blood from a limb extremity toward the heart of a patient it accomplishes the exact opposite of the instant invention which is designed to engorge a vein toward the extremity of a limb by milking not only any small amount of venous blood toward the limb extremity but also milking deeper level arterial blood toward the extremity. Further, the Tillander apparatus substantially totally encloses the portion of the limb to which it is applied, thereby preventing any access to an underlying vein. Further, because of the shape of the Tillander apparatus it is not reversible on the extremity for operation in emptying blood from a limb toward the extremity thereof.

BRIEF DESCRIPTION OF THE INVENTION

The tourniquet of the instant invention comprises an annulus constructed of flexible, resilient material to be initially applied about the proximal end of the limb of a patient adjacent his torso. The tourniquet applies heavy radial inward pressure on the limb throughout a zone extending circumferentially thereabout and may be rolled downwardly along the limb toward the free extremity thereof independent of any sliding action of the tourniquet relative to the skin of the limb. By this action, even though a patient has substantially no cardiac output, the blood downward along the limb from the tourniquet is "milked" not only through the veins of the limb but also downwardly through the deeper underlying arteries of the limb with the result that a vein toward the free end of the limb will be engorged with blood and hyperextended for ease in starting intravenous therapy.

When cardiac output is minimal or even nonexistent, the veins closer to the surface of the skin have substantially no blood therein and are substantially fully collapsed, the only blood within the limb to any extent being the blood within the deeper underlying arteries. Accordingly, the tourniquet of the instant invention does not act in the manner of a conventional tourniquet which only prevents return flow of blood through the veins toward the heart. Rather, the rolling tourniquet of the instant invention creates sufficient radial inward pressure on a limb throughout a circumferential zone thereof and is moveable down the limb in a manner such that the blood remaining in deeper underlying arteries is "milked" downwardly along the limb for ultimate hyperextension of a near the surface vein.

The relatively heavy radial inward pressure exerted by the tourniquet of the instant invention is of course even more critical when the patient is an overweight patient and sufficient pressure must be brought to bear on arteries below reasonably thick layers of fat.

The main object of this invention is to provide a means whereby a vein in the limb of a patient may be engorged with blood and thus hyperextended for ease in initiating intravenous therapy, even when the patient has substantially no cardiac output.

Another object of this invention is to provide a tourniquet constructed in a manner whereby it may be operative to apply radial inward pressure on an associated limb throughout a zone extending completely about the limb and with the tourniquet subsequentially being rollable downwardly along the limb toward the free extremity thereof in order to thereby "milk" arterial as well as venous blood in the limb downwardly toward the free extremity thereof for the purpose of engorging a lower vein of the limb with blood in order that such vein may be hyperextended for ease of starting intravenous therapy.

Yet another object of this invention is to provide a tourniquet which may be readily applied to a patient.

Still another object of this invention is to provide a tourniquet which may be readily removed from a patient through the utilization of only one hand of a person attending the patient.

Still another important object of this invention is to provide a rolling tourniquet that may be readily constructed in different lengths and thicknesses for utilization on different size patients.

A final object of this invention to be specifically enumerated herein is to provide a tourniquet in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully described and claimed, reference being had to the accompanying drawings forming a part hereof, wherein like numerals refer to like parts throughout.

DESCRIPTION OF THE PREFERRED EMBODIMENT

Figure 1:
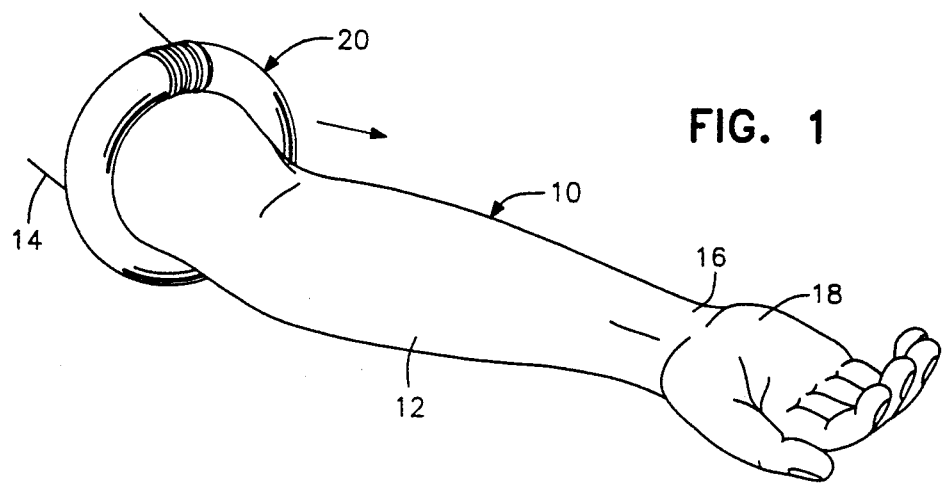
FIG. 1 is a fragmentary perspective view of the lower arm portion of a patient with a tourniquet constructed in accordance with the present invention disposed about the arm above the elbow thereof preparatory to the tourniquet being rolled downwardly along the arm.
Figure 2:
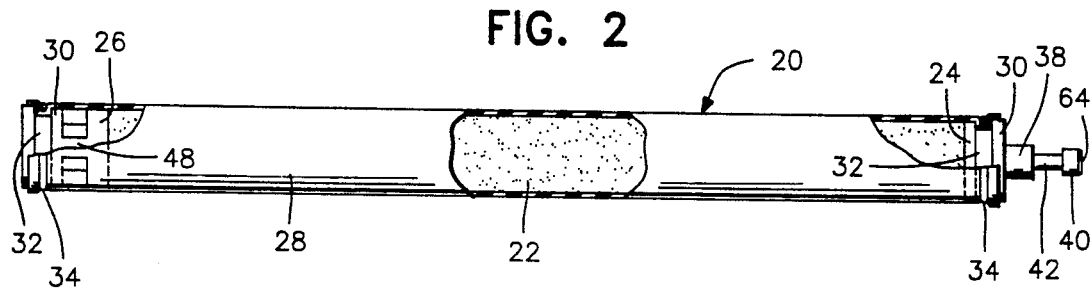
FIG. 2 is an elevational view of the tourniquet illustrated in FIG. 1 in a straightened condition with the ends thereof disengaged from each other and portions of the tourniquet being broken away and illustrated in vertical section in order to illustrate the structural details thereof.

Referring now more specifically to FIGS. 1 and 2, a patient's arm is fragmentarily illustrated in FIG. 1 and referred to in general by the reference numeral 10. The arm 10 includes the lower forearm portion 12, the upper arm portion 14 and the wrist 16 connecting the patient's hand 18 to his lower forearm portion 12.

The rolling tourniquet of the instant invention is referred to in general by the reference numeral 20 and is illustrated in FIG. 1 as applied about the upper arm portion 14 preparatory to being rolled down the arm 10 toward the wrist 16. From FIG. 2 of the drawings it may be seen that the rolling tourniquet 20 comprises an inner cylindrical body 22 constructed of soft open cell foam rubber of ten durometer. The opposite ends of the cylindrical body 22 have end fittings 24 and 26 abutted thereagainst. The cylindrical body is enclosed within latex rubber tubing 28 of thirty durometer and each of the fittings 24 and 26 includes a cylindrical portion 30 provided with a circumferential groove 32 in which the corresponding ends of the tubing 28 are secured by tight fitting O-rings 34 tightly crimping the tube ends 28 within the groove 32.

Figure 3:
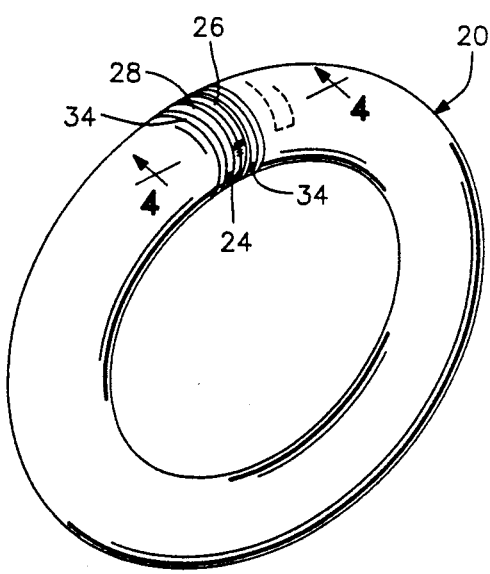
FIG. 3 is an enlarged perspective view of the tourniquet.

The cylindrical body 22, when not encased within the tubing 28, is generally two inches in diameter and the tubing 28 is generally three-quarter inches in diameter. However, the length of the cylindrical body 22, when in a relaxed state, is generally twice the length of the tubing 28. Accordingly, the tubing 28 is longitudinally stretched to approximately twice its length and, therefore, does not crimp on its inner periphery when the end fittings 24 and 26 are joined together in the manner illustrated in FIGS. 1 and 3 of the drawings. Further, the radial compression of the cylindrical body from a relaxed diametric dimension of approximately two inches to a radially compressed dimension of slightly less than three-quarters of an inch greatly increases the density of the cylindrical body 22 and resists foreshortening thereof as a result of the tubing 28 being disposed thereover in a stretched condition approximately two times its relaxed length.

It will be noted that the length of the complete tourniquet as illustrated in FIG. 2 will vary according to the age, size or heaviness of the patient upon whom the tourniquet 20 is to be used. The tourniquet 20, in its condition illustrated in FIG. 2, will be between three-quarter inch and one inch in diameter although a considerably smaller diameter tourniquet could be used on infants, in the neighborhood of generally one quarter inch in diameter, and larger diameter tourniquets 20 on the order of one and one half inches in diameter may be used on larger heavier persons.

Still further, medical grade polymer with a durometer of ten may be used in lieu of the open cell foam rubber comprising the cylindrical body 22. Such polymers are manufactured under the names "OREFLEX", "SECOFLEX" and "DURUFLEX". When such polymers are used, they may be covered with a tubing such as the tubing 28, but these polymers are capable of being stretched two to two and one half times their length.

Figure 4:
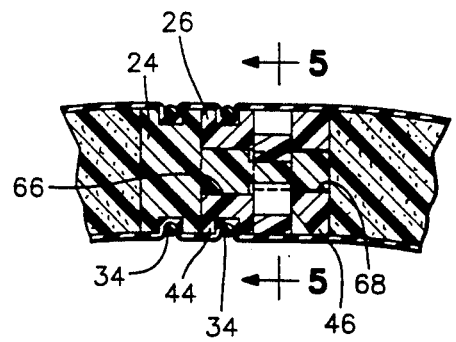
FIG. 4 is an enlarged fragmentary sectional view taken substantially upon the plane indicated by the section line 4—4 of FIG. 3.
Figure 5:
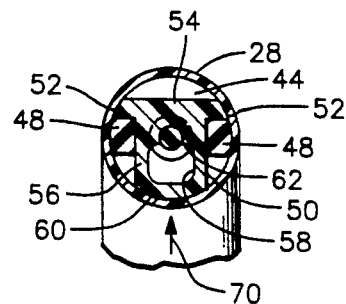
FIG. 5 is a sectional view taken substantially upon the plane indicated by the section line 5—5 of FIG. 4.

With attention now invited more specifically to FIGS. 4 and 5 of the drawings, it may be seen that the end fitting 24 includes a central axially projecting pin 38 having a slightly reduced outer end head 40 and an intermediate length circumferential groove 42. On the other hand, the end fitting 26 comprises a cylindrical body having first and second end portions 44 and 46 interconnected by opposite side axially extending portions 48. In addition, a T-shaped slide 50 including beveled surfaces 52 at the opposite ends of its cross head 54 and its leg 56 provided with a keyhole opening 58, the beveled (and slightly rounded) surfaces 52 and the free end edge 60 of the leg 56 comprising arc segments of the same circle corresponding with the inner surface of the tube 28. Thus, the resiliency of the tube 28 tends to maintain the slide 50 in the position thereof illustrated in FIG. 5 with the groove 42 snugly received within the narrow portion 62 of the keyhole opening 58.

The end extremity of the head 40 is slightly bevelled as at 64 and the pin thus may be inserted inwardly through the registered central bores 66 and 68 formed through the end portions 44 and 46 with the bevelled surface being operable to upwardly cam the slide 50 from the position thereof illustrated in FIG. 5 to a position such that the head 40 may be received through the wider lower portion of the keyhole opening 58 with the groove 48 registered with the slide 50. Then, the resiliency of the tube 28 returns the slide 50 to the position thereof illustrated in FIG. 5 with the groove 62 received in the narrow portion 62 of the slide 58. Thus, the ends of the tourniquet may be readily joined together.

When it is desired to release the ends of the tourniquet, it is merely necessary to apply an upward force in the direction of arrow in FIG. 5 on the free end of the leg 56 in order to register the wider lower portion of the opening 58 with the head 40, thus allowing the end fittings 24 and 26 to be readily separated. Of course, if the rolling tourniquet 20 is disposed about a patient's arm in a stretched condition, mere upward displacement of the slide 50 to release the head 40 from the slide 50 will automatically cause axial separation of the fittings 24 and 26. In this manner, a person attending a patient and wishing to remove the tourniquet 20 may do so with only one hand.

In operation, and assuming that a patient has substantially no cardiac output, the veins of the arm closer to the surface thereof are substantially fully collapsed and do not have sufficient blood therein to be "milked" downwardly along the arm to the area of the wrist 16 in order to engorge or hyperextend a wrist vein sufficiently to initiate intravenous therapy. However, when the rolling tourniquet 20 is lengthwise stretched and secured about the upper arm portion 14 as illustrated in FIG. 1 of the drawings, the rolling tourniquet 20 exerts a strong radial inward force on the upper arm sufficient to compress not only the veins of the arm reasonably close to the outer surfaces thereof but also the underlying arteries which have blood pooled therein. Then, the rolling tourniquet 20 is slowly rolled down the arm 10 toward the wrist 16 over a generally five second period of time with the result that the strong radial inward pressure exerted on the arm 10 by the stretched and flexible rolling tourniquet 20 compresses not only the veins but also the underlying arteries as the rolling tourniquet moves downwardly along the arm. In this manner, the blood pooled within the arteries and any small quantity of blood remaining in the veins is milked downwardly therethrough toward the wrist with the result that the arterial blood continues through the arterioles, capillaries, venules and then into the veins distal to the tourniquet 20. Then, as the tourniquet 20 approaches the wrist 16, this blood engorges the veins at and adjacent the wrist such that they become hyperextended to the extent that a needle may be readily introduced thereinto for the purpose of intravenous therapy.

Of course, once the needle is introduced into a hyperextended vein, finger pressure is applied to the free end of the leg 56 of the slide 50 in order to release the end fittings 24 and 26 from each other and the end fittings 24 and 26 are thus readily separated by the use of only one hand.

Again, it is herein stressed that the rolling tourniquet 20 will be constructed of different lengths and diameters according to the age and bulk of the patient upon which the rolling tourniquet is to be used. Once the correct size and strength of rolling tourniquet 20 is used, the constant heavy radial inward pressure on the associated arm throughout a cirucumferential zone of the arm and gradually moved down the arm toward the wrist 16 is sufficient to hyperextend a vein at or adjacent the wrist 16 sufficient to be readily located and have a needle introduced thereinto for the purpose of intravenous therapy.

In addition to utilizing foam rubber in the construction of the cylindrical body 22 and also medical grade polymer material having a ten durometer rating, the cylindrical body could be replaced by a body comprising a plurality of side-by-side or even woven rubber strips such as those used in "Bingy Cords". However, the tubing 28 must be stretched sufficient to prevent kinking or folding of the inner circumferential portions of the rolling tourniquet 20 as it is rolled downwardly along the arm 10.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalence may be resorted to, falling within the scope of the invention.

What is claimed as new is as follows:

1. A tourniquet for initial securement about proximal portion of a body limb and gradual rolling down along the limb, said tourniquet comprising an elongated, generally straight, cylindrical member having opposite ends and constructed of flexible, elastic material and having circumferentially joined exterior longitudinal wall portions, the longitudinal ends of said cylindrical member being provided with coacting connecting end fittings for releasably connecting said ends together in end aligned relation, said longitudinal wall portions of said annular member being generally straight and of substantially the same length when said longitudinal wall portions are relaxed in their static state, said cylindrical member consisting of a longitudinally straight internal body of radially inwardly and longitudinally compressed resilient foam material and a lengthwise and radially outwardly stretched flexible and resilient covering tube forming said wall portions disposed over said body, the opposite ends of said body having said coacting end fittings mounted thereon and to which the opposite ends of said covering tube are anchored, said fittings being releasably engageable with each other when said tourniquet is manipulated into a generally annular configuration with said fittings being operable to releasably secure the opposite ends of said body together in axially aligned relation.

2. The tourniquet of claim 1 wherein said cylindrical member is between one quarter inch and one and one half inches in diameter when said cylindrical member is in said static state.

3. The tourniquet of claim 1 wherein said end fittings are generally cylindrical in configuration and include circumferential grooves in which the opposite ends of said covering tube are secured.

4. The method of causing lower veins of a person's limb to be hyperextended for enabling intravenous therapy to be readily initiated with a minimum loss of time, even when the person has little or no cardiac output, initially applying a heavy generally radial inward force on a proximal portion of said limb throughout at least substantially the full length of a zone extending about said limb with the inward pressure being applied through out said zone being sufficient to locally compress not only veins closely beneath the skin surface but also sufficient to locally compress arteries of the limb further beneath the skin surface, and moving said zone, gradually, downwardly along said limb at a linear speed effective to "milk" both venous blood and arterial blood within said limb proximal to said zone toward the free end of the limb, whereby to hyperextend at least one vein within the free end portion of the limb.

5. The method of claim 4 wherein the step of gradually moving said zone downwardly along said limb is effected substantially independent of sliding frictional engagement with said limb.

6. The method of claim 5 wherein the step of applying a heavy generally radial inward pressure on said limb includes the step of installing a flexible and resilient annulus about a proximal portion of said limb in a circumferential stretched condition and with the contact area of said annulus with said limb comprising said zone, and the step of gradually moving said zone downwardly along said limb includes gradually rolling said annulus downwardly along said limb.

7. The method of causing the lower veins of a person's limb to be hyperextended for enabling intravenous therapy to be initiated with minimum difficulty and loss of time, even when the person has little or no cardiac output, said method comprising initially applying a circumferentially stretched, flexible and resilient annulus about a proximal portion of said limb developing heavy generally radially inward pressure on said limb sufficient to locally compress not only veins of the limb closely beneath the skin surface but also sufficient to locally compress arteries of the limb further beneath the skin surface, and gradually rolling said annulus downwardly along said limb toward the free end thereof.

8. The method of claim 7 wherein said annulus is substantially constant in diameter throughout its circumferential extent and the diameter of said annulus is between one-quarter of an inch and one and one-half inches.

* * * * *